(12) United States Patent
Champaigne et al.

(10) Patent No.: US 10,451,464 B1
(45) Date of Patent: Oct. 22, 2019

(54) CAPACITIVE SENSOR FOR A FLOW CONTROL VALVE

(71) Applicant: Electronics Inc., Mishawaka, IN (US)

(72) Inventors: Jack M. Champaigne, Mishawaka, IN (US); Mark A. Ingram, Granger, IN (US)

( * ) Notice: Subject to any disclaimer, the term of this patent is extended or adjusted under 35 U.S.C. 154(b) by 0 days.

(21) Appl. No.: 16/354,370

(22) Filed: Mar. 15, 2019

Related U.S. Application Data

(63) Continuation-in-part of application No. 16/055,136, filed on Aug. 5, 2018, now Pat. No. 10,253,901.

(51) Int. Cl.
| | | |
|---|---|---|
| *G01F 1/74* | (2006.01) | |
| *G01F 1/64* | (2006.01) | |
| *G01N 15/10* | (2006.01) | |
| *G01F 1/78* | (2006.01) | |
| *F16K 27/04* | (2006.01) | |
| *F16K 31/08* | (2006.01) | |
| *F16K 31/10* | (2006.01) | |
| *F16K 1/12* | (2006.01) | |
| *A01C 7/10* | (2006.01) | |

(52) U.S. Cl.
CPC ............ *G01F 1/74* (2013.01); *A01C 7/105* (2013.01); *F16K 1/123* (2013.01); *F16K 27/048* (2013.01); *F16K 31/086* (2013.01); *F16K 31/10* (2013.01); *G01F 1/64* (2013.01); *G01F 1/785* (2013.01); *G01N 15/1031* (2013.01)

(58) Field of Classification Search
CPC .. G01F 1/64; G01F 1/74; G01F 1/785; G01N 15/1031; A01C 7/105
See application file for complete search history.

(56) References Cited

U.S. PATENT DOCUMENTS

| | | | | |
|---|---|---|---|---|
| 1,477,722 | A * | 12/1923 | Slattery ................... | F16K 1/123 137/219 |
| 3,635,082 | A * | 1/1972 | Prellwitz ................. | G01F 1/712 324/684 |
| 4,592,240 | A | 6/1986 | McHale et al. | |
| 4,614,100 | A | 9/1986 | Green et al. | |
| 4,930,356 | A | 6/1990 | Porges | |
| 5,159,949 | A ‡ | 11/1992 | Prescott .................. | F15B 5/003 137/82 |
| 5,176,018 | A | 6/1993 | Thompson | |
| 5,435,337 | A ‡ | 7/1995 | Kemp .................... | F16K 15/025 137/219 |
| 5,459,406 | A | 10/1995 | Louge | |
| 5,808,242 | A | 9/1998 | Satake et al. | |
| 5,929,343 | A | 7/1999 | Yamamoto et al. | |
| 7,503,227 | B2 * | 3/2009 | Davis ........................ | G01F 1/66 73/861.42 |

(Continued)

*Primary Examiner* — Atif H Chaudry
(74) *Attorney, Agent, or Firm* — Botkin & Hall, LLP

(57) ABSTRACT

A flow sensor for use downstream from a particulate media dispensing device is provided having an inlet to receive particulate media and an outlet to dispense the media. The flow sensor has an inlet portion with a funnel to direct particulate media towards a central axis. An axially mounted flow director is located downstream from the funnel to direct the media outwards towards a sensor portion. A capacitive sensor located in the sensor portion surrounds the flow director to create an annular flow path to measure the amount of media that passes through sensor rings in the sensor.

18 Claims, 15 Drawing Sheets

(56) References Cited

U.S. PATENT DOCUMENTS

| | | |
|---|---|---|
| 8,061,217 B2 | 11/2011 | Hisada et al. |
| 9,022,063 B2 | 5/2015 | Powell |
| 10,253,901 B1 * | 4/2019 | Champaigne ....... F16K 31/0655 |
| 2010/0148804 A1 * | 6/2010 | Jakoby ................... G01F 1/662 |
| | | 324/663 |
| 2011/0118098 A1 ‡ | 5/2011 | Harms ................. B05C 5/0279 |
| | | 493/2 |
| 2011/0259120 A1 * | 10/2011 | Thonstad ................ G01F 1/363 |
| | | 73/861.42 |
| 2012/0061596 A1 ‡ | 3/2012 | Hensel ................... F02C 7/232 |
| | | 251/65 |
| 2015/0122015 A1 * | 5/2015 | Leppard ............... G01F 23/263 |
| | | 736/304 C |
| 2015/0300851 A1 ‡ | 10/2015 | Isik-Uppenkamp .... G01F 1/584 |
| | | 73/861.12 |
| 2017/0227131 A1 ‡ | 8/2017 | Herold ..................... F16K 1/12 |
| 2018/0264625 A1 | 9/2018 | Schneidau |

\* cited by examiner
‡ imported from a related application

CAPACITIVE SENSOR FOR A FLOW CONTROL VALVE

CROSS REFERENCE TO RELATED APPLICATIONS

This application is a Continuation-in-Part of U.S. application Ser. No. 16/055,136 filed Aug. 5, 2018, the disclosure of which is hereby incorporated by reference.

BACKGROUND OF THE INVENTION

This present disclosure relates to flow control valves that control the flow of particulate, such as is used in media blasting, shot peening, or other systems where the user desires to control the flow of different types of flowable particulate and sense the amount passing through the valve. Existing flowable particulate valves in the art suffer from complexity, manufacturability, and functionality issues. Most valves use a fixed orifice and a movable pintle that retracts to allow media to flow. The pintle is spring-loaded to bias it towards the closed position, creating issues for assembly and maintenance. The spring can wear, break, or become damaged, creating functionality issues. When actuated, the pintle can bounce, creating control problems. Another problem is having closed loop control of the valve by knowing exactly the amount of media that is being dispensed. Other designs use a deflected beam as a means to measure, while others use optical or other sensing technology. An improved valve with media sensing is needed.

Other applications utilize an upstream flow valve that lacks the ability to measure the flow of particulate. This can result in poor flow control in systems that lack a true measurement of the particulate flow. Some flow sensors rely on the displacement of an arm as the media drops down on to it, while others use a non-contacting sensor style. These sensors have difficulty in measuring flow, particularly as the type of media changes or when the flow stream is unpredictable (i.e. when it moves from side to side in the flow path). An improved flow sensor is needed.

SUMMARY OF THE INVENTION

The present disclosure describes a valve designed to regulate the flow of a particulate media. The valve has an inlet portion that funnels the particulate media down through the center of the valve. The inlet portion has repelling magnets and a shield. The shield reduces the magnetic field from the magnet that passes through the center of the valve. The inlet portion has a shuttle sleeve that carries the particulate media on the inside. Surrounding the outside of the shuttle sleeve is a movable shuttle. The shuttle has shuttle magnets and a magnetic shield that reduces the magnetic field from the magnets that passes through the center of the valve. The shuttle has a movable orifice attached to it that contacts a flow director. The flow director is located in the outlet portion and channels the media past a flow sensor to detect the amount of particulate being dispensed. A portion of the valve is made from a metal, such as brass or copper that interacts with the shuttle magnets to generate eddy currents when the shuttle is in motion. The eddy currents act to dampen the movement of the shuttle.

A capacitive flow sensor uses sensing rings in conjunction with a fixed flow director. The flow sensor uses a funnel portion near or at an inlet to direct flow towards the center. Located in the flow path after the funnel portion is the fixed flow director that directs the particulate outwardly towards the inside surface of the tube and therefore the sensing rings. The funnel and fixed flow director create an indirect and uninterrupted flow path that slows the flow of particulate and creates accurate sensing of particulate. The signal from the flow sensor can be used to regulate or control an upstream valve for particulate.

DESCRIPTION OF THE PREFERRED EMBODIMENT

Figure 1:
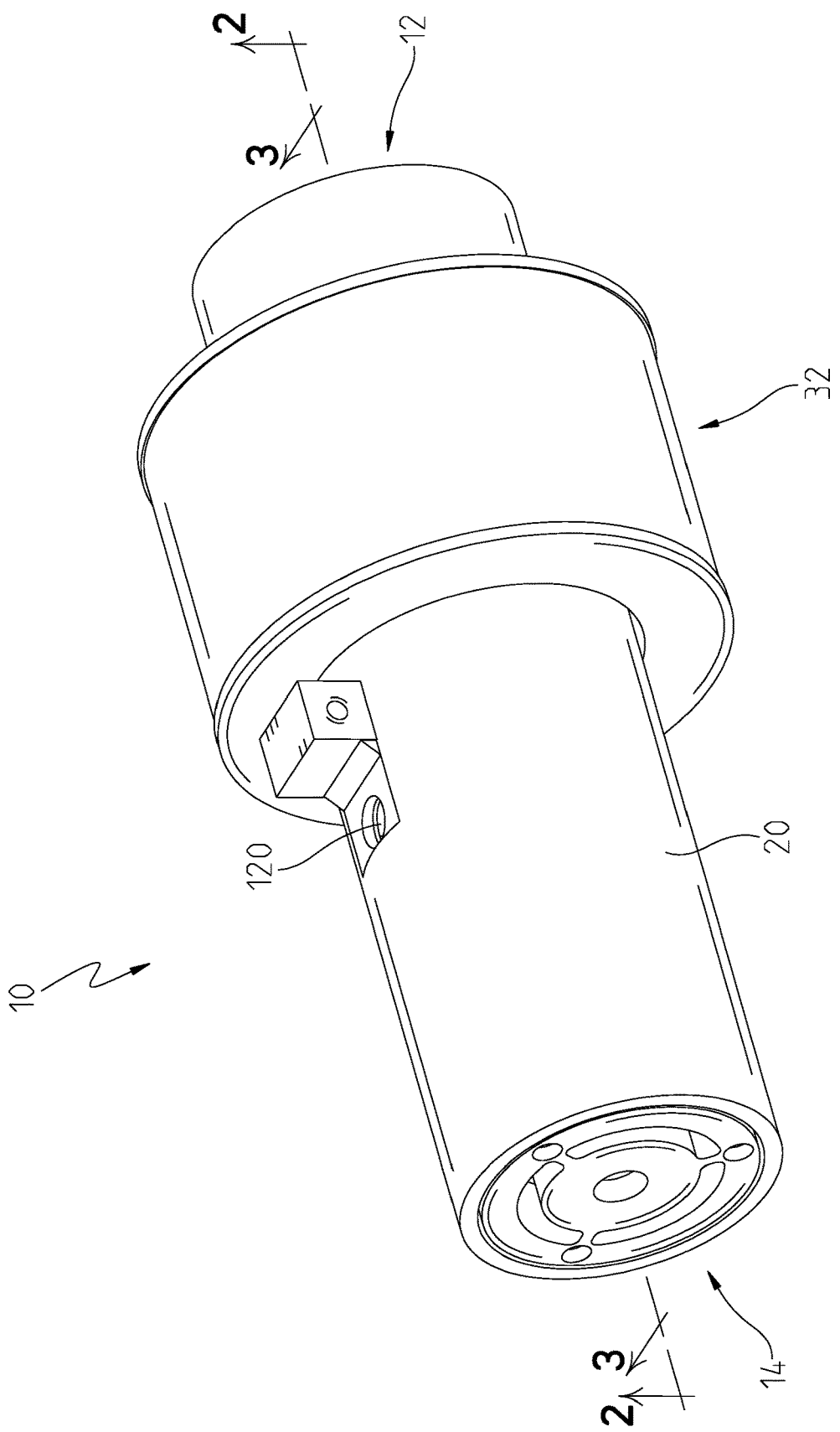
FIG. 1 is an isometric view of the valve.
Figure 2:
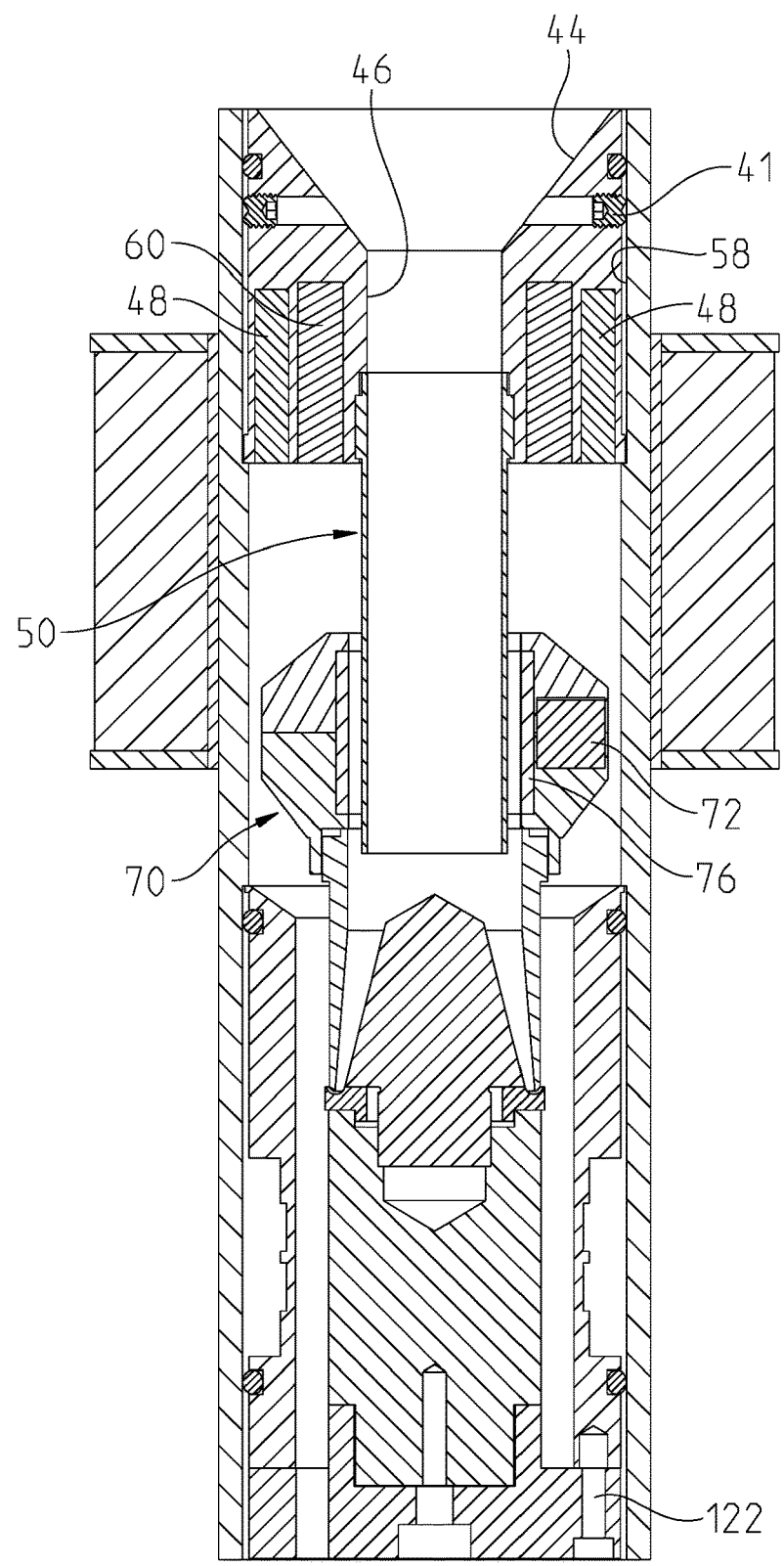
FIG. 2 is a section view 2-2 of the valve in FIG. 1.
Figure 3:
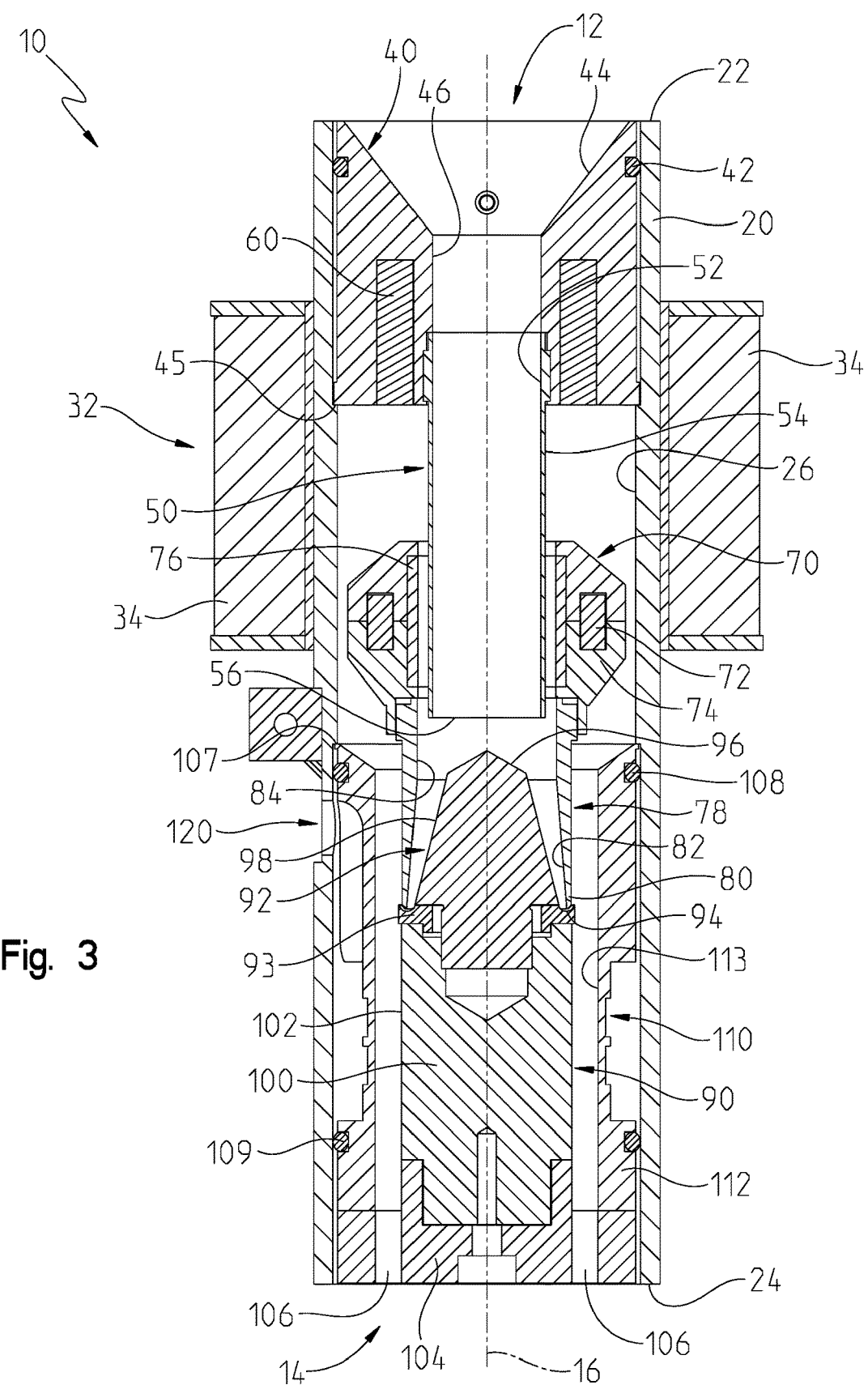
FIG. 3 is a section view 3-3 of the valve in FIG. 1 showing the shuttle in the closed position.
Figure 4:
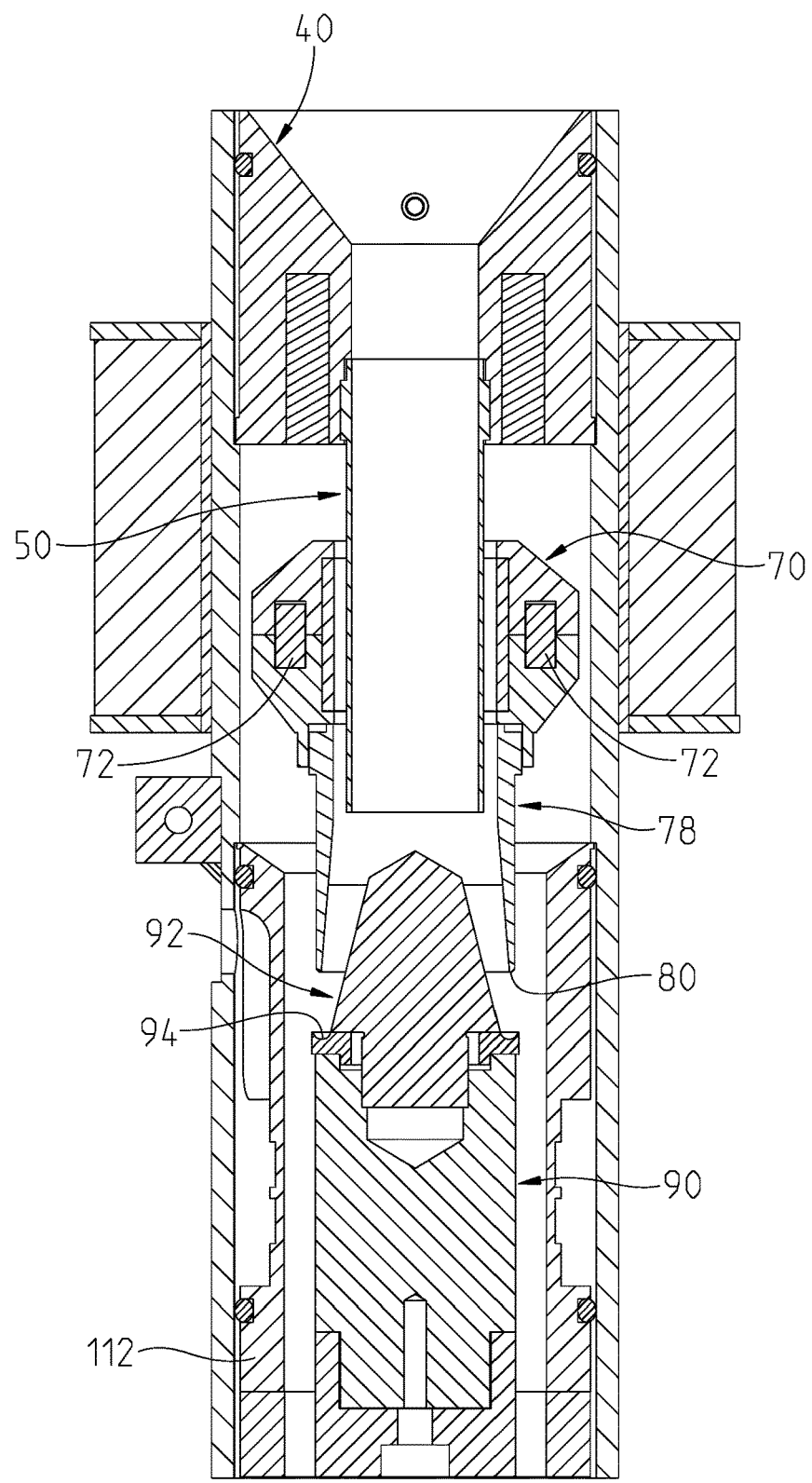
FIG. 4 is a section view of the valve in FIG. 3 showing the shuttle in the open position.

An electrically operated valve 10 is shown in FIGS. 1-8 with an inlet 12 and an outlet 14. The valve 10 is designed to regulate the flow of particulate media that is not ferromagnetic. The particulate media is flowable, commonly a blasting media such as glass, plastic, aluminum oxide, or other particulate. In other words, particulate media made from steel or alloys of Iron are not commonly used with the valve 10. The particulate media is loaded into the inlet 12, commonly from a hopper or other storage vessel (not shown). The valve 10 is operable between an opened state and a closed state. The opened state allows particulate media to flow from the inlet 12 to the outlet 14, while the closed state blocks the particulate media from flowing. The valve 10 can operate in positions between the open and closed positions in order to regulate the flow of particulate media.

The valve 10 has a tube 20 that is shown as a hollow cylindrical tube with a consistent wall thickness, but other structures are contemplated, such as a square, rectangular, or other elongate hollow component that allows a flow path. The inlet 12 is located near a top edge 22 and the outlet 14 is located near a bottom edge 24. The tube 20 may be threaded at its ends or have a feature to allow it to attach to other containers, tubes, or devices. The valve 10 has a central axis 16 that is located at the center of the tube 20. The tube 20 has an inside surface 26 where other components contact or seal against. The tube 20 in the embodiment described herein is formed from copper or a copper alloy, such as brass or bronze. The tube 20 may also be made from aluminum or other material that is electrically conductive or responds to a changing magnetic field.

A coil 32 surrounds the tube 20 that is also fixed with respect to the tube 20. The coil 32 has windings 34 that generate a magnetic field when energized. The valve 10 may include a housing (not shown) that surrounds a portion of the tube 20 and includes controls, wiring, and circuit boards.

A funnel 40 is located adjacent the top edge 22 and is shown as centered about the central axis 16. A seal 42 seals the funnel 40 to the inside surface 26 of the tube 20. The funnel 40 has a wide open mouth with an inside surface 44 that narrows down to a cylindrical surface 46. The inside surface 44 is conical in nature but the device is not limited to that shape. It is contemplated that the inside surface 44 of the funnel 40 is straight and any funnel or conical feature is externally located above the valve 10. The funnel 40 may also be considered as an inlet portion. The funnel 40 is axially located in the tube 20 by a step surface 45 and includes set screws 41 that impinge against the tube 20 and prevent movement of the funnel 40 with respect to the tube 20. The funnel 40 includes repelling magnets 48 that are equally spaced around the cylindrical surface 46. The repelling magnets 48 are pressed into place or otherwise secured with adhesive or fasteners that prevents the magnets 48 from falling out or becoming loose. The funnel 40 is made from a non-magnetic material, such as plastic, aluminum, ceramic, or other material that does not short out or conduct the magnetic field from the repelling magnets 48. The inside surface 44 and cylindrical surface 46 cooperate to direct particulate to the inside of a shuttle sleeve 50. The shuttle sleeve 50 is a cylindrical tubular component, made from a non-magnetic material such as plastic or aluminum, with an inside surface 52 and outside surface 54. The shuttle sleeve 50 is secured to the funnel 40 through a press fit, threading, or other attachment method that affixes the two components. The shuttle sleeve 50 is centered about the central axis 16 and has a terminal edge 56 that is opposite the open mouth. To maintain the coaxial position of shuttle sleeve 50 to the central axis 16, a skirt surface 58 that is closely matched to the inside surface 26 of the tube 20 extends down from the open mouth to the top of the shuttle sleeve 50. Adjacent the repelling magnets 48 is a funnel shield 60 that conducts magnetic field from the repelling magnets 48 to keep the magnetic field away from the inside flow path of the funnel 40. Because ferrous or other particulates with magnetic attraction may pass through the flow path, a strong enough magnetic field in the flow path would create an undesirable buildup of these particles that would impede flow of the particulate media. The funnel shield 60 shunts the field to the point that ferrous or magnetic particles do not accumulate.

A shuttle 70 is located around the shuttle sleeve 50 and also centered about the central axis 16. The shuttle 70 is hollow and slidable along the outside surface 54 of the shuttle sleeve 50 between an open position (shown in FIG. 4) and a closed position (shown in FIG. 3). The shuttle 70 has shuttle magnets 72 that are contained in a shuttle body 74. The shuttle body 74 is made from a non-ferromagnetic material, such as plastic, aluminum, ceramic, or other material that does not short out or conduct the magnetic field of the shuttle magnets 72, and includes a shuttle magnet shield 76 that is located adjacent the shuttle magnets 72 and closer to the central axis 16. The shuttle magnet shield 76 shunts the magnetic field generated by the shuttle magnets 72 that could attract ferrous particles or other particles. The particles may be attracted to a magnetic field and build up on the shuttle sleeve 50 or the shuttle 70, or get stuck between the shuttle body 74 and shuttle sleeve 50. Extending from the lower portion of the shuttle body 74 and affixed thereto is a movable orifice 78. The movable orifice 78 is a tubular component with a terminal sealing edge 80, shown in FIG. 4. In the embodiment described herein, the movable orifice 78 is made from metal (such as aluminum), but other materials are contemplated. The movable orifice 78 includes a tapered surface 82 located on the inside that extends from the inside surface 84. The media flows from the shuttle sleeve 50 and into the inside of the movable orifice 78. The tapered surface 82 may include other features designed to modify the flow properties of the particulate media, such as channels, different angles, or additional surfaces. To remove the shuttle 70 for maintenance, cleaning, or exchange the movable orifice 78, the user removes the funnel 40 and shuttle sleeve 50 and lifts the shuttle 70 out through the top of the tube 20.

A fixed flow director 90 is affixed to the tube 20 near the bottom edge 24 and is also centered about the central axis 16. The flow director 90 has a removable cone portion 92 with a replaceable seal 93 having a sealing surface 94. The terminal edge 56 of the shuttle sleeve 50 is spaced above the sealing surface 94 and the two are a fixed distance apart. In the embodiment described herein, the replaceable seal 93 is made from steel, but other materials are contemplated. The sealing surface 94 is groove-shaped to receive and locate the terminal sealing edge 80 on the shuttle 70. It is held between the cone portion 92 and the flow directing portion 100, which may be press fit or threaded. The cone portion 92, as shown, is tapered with a top and conical surface 96, 98. The cone portion 92 may be parabolic, curved, or straight, depending on the properties of the particulate media that may be used. The flow directing portion 100 has an outer diameter surface 102. A mounting base 104 locates the fixed flow director 90 to be aligned with the central axis 16 and allows flow through it via arcuate apertures 106. The cone portion 92 and sealing surface 94 is designed to mate with the movable orifice 78 and the terminal sealing edge 80 to open or close a flow path between the funnel 40 and flow directing portion 100. The fixed flow director 90 is separable from the base 104 to allow different cone portion 92 and flow directing portions 100 to be exchanged for different desired flow properties of the particulate media. The flow director 90 may have a different shape than the flow director 90 shown in FIG. 3. The purpose of the flow director 90 is to direct media outwardly from a central region of the tube 20 and toward the inside surface 26 of the tube 20. For instance, it is not necessary that the flow director 90 have a cone portion 92. The flow directing portion 100 of the flow director 90 will prevent media from being located in the central region of tube 20, which corresponds to areas of the tube 26 that adjacent to the central axis 16 of the tube 26.

The absence of an applied magnetic field from the coil 32, gravity, and the repelling magnets 48 result in the shuttle 70 resting in the closed position where it contacts the fixed flow director 90. Additionally, if it is desired that shuttle 70 be closed quickly, the polarity on the coil 32 may be reversed so that the coil 32 drives the shuttle 70 downward. In the closed position, shown in FIG. 5A, the movable orifice 78 contacts and seals against the sealing surface 94 and particulate media does not flow. As an electrical current is applied to the coil 32, the shuttle 70 begins to move away from the fixed flow director 90, such as shown in FIG. 5B. Due to the shape of the cone portion 92 and tapered surface 82, the distance the shuttle 70 moves away from the cone portion 92 creates a variable gap for the particulate media to pass through. Increasing the amount of energy applied to the coil 32 increases the amount that the shuttle 70 moves away from the closed position.

A flow sensor 110 surrounds the fixed flow director 90 that detects the amount of particulate media that is passing between the outer diameter surface 102 and flow sensor 110. The flow sensor 110 is shown as located and attached to a flow sensor body 112. The flow sensor body 112 is located between the mounting base 104 and a step 107 in the tube 20. The flow sensor body 112 is sealed to the tube 20 with seals 108, 109 and has a lead-in surface 111. The lead-in surface 111 is angled and directs any media into the flow path. The sensor 110 is capacitive and includes sensor rings 114, 116 that sense movement of the particulate media adjacent the sensor rings 114, 116. The sensor rings 114, 116 are near the inside surface 26 of the tube 20. Wires connect the sensor rings 114, 116 to an external circuit through a channel 118 in the sensor body 112 and out through the wire egress 120. The external circuit is commonly located inside the housing (not shown) and can be used by the valve 10 for closed loop control of the shuttle 70. The flow sensor 110 and sensor body 112 are secured to the tube 20 using fasteners, adhesive, or other method. The mounting base 104 is secured through fasteners 122. Removing the fasteners 122 allows the mounting base 104, flow directing portion 100, cone portion 92, and replaceable seal 93 to be removed for maintenance, cleaning, or component exchange for a different media. The flow sensor 110 is shown as using sensor rings 114, 116 that are adjacent the flow path for the particulate media, but it is contemplated that other sensor designs are used. To obtain a reliable signal for detecting media, within the flow sensor 110, it is desirable to have the media near the sensor rings 114, 116. For this reason, the flow director 90 directs media relatively near the sensor rings and away from the central axis 16 of the tube 20, where the media would be relatively far from the sensor rings. If sensor configurations not using capacitive elements such as rings 114, 116 are employed, it is desirable for the media to be located near the capacitive elements and the flow diverter 90 serves that purpose. As an alternative embodiment for a sensor could be the use of one sensor ring is located in the flow sensor body 112, and the other ring is located in the flow directing portion 100. In such a case, it is still desirable that media be predictably directed by the flow director 90 to consistently locate the flow path of media between and near capacitive elements. It is further contemplated that the flow directing portion 100 may be made from a material that conducts and connects to the external circuit 118 to form part of the sensor 110.

The repelling magnets 48 in the funnel 40 have a north-south orientation that puts the magnetic field as it exits the magnet parallel to the central axis 16. Some of the field is conducted through the funnel shield 60. The shuttle magnets 72 are aligned in a similar fashion such that the magnetic field as it exits the magnet is parallel to the central axis 16, with some of the field conducted through the shuttle magnet shield 76. The shuttle magnets 72 and repelling magnets 48 have identical facing poles and generate an increasing repelling force as they are brought closer to each other. For example, if the shuttle magnets 72 have a north pole that faces the repelling magnets 48, the repelling magnets would be oriented to have a north pole that faces the shuttle magnets 72. The repelling force generated by the magnets 48, 72 acts like a spring that biases the shuttle 70 away from the funnel 40. Because of the biased force from the magnets 48, 72, no spring is required. Ordinarily, a valve would require a spring to ensure the shuttle returns to the closed position when the electric current is removed.

When an electric current is passed through the windings 34 in the coil 32, a magnetic field is generated that draws the shuttle 70 towards the funnel 40, which separates the terminal sealing edge 80 from the sealing surface 94. The greater the electrical current that is passed through the coil 32, the greater the magnetic force is that is applied to the shuttle 70, which causes it to move closer to the funnel 40. As the shuttle 70 gets closer to the funnel 40, the repelling magnets 48 begin to counteract the magnetic force from the coil 32. When a magnetic field is generated by the coil 32, the response from the shuttle 70 is non-linear due to the exponential increase of magnetic field over decreased distance. This means that when the shuttle 70 moves closer to the desired position, the amount of magnetic field needed to position the shuttle 70 would be less than what was generated to move it from its closed and resting position, resulting in the shuttle 70 moving past the desired position. By adding in the repelling magnets 48, magnetic force repelling the shuttle 70 counteracts the natural increase of force as the shuttle moves closer to the coil 32. With this, the shuttle position is more proportional to the amount of electrical current provided to the coil 32.

Figure 9:
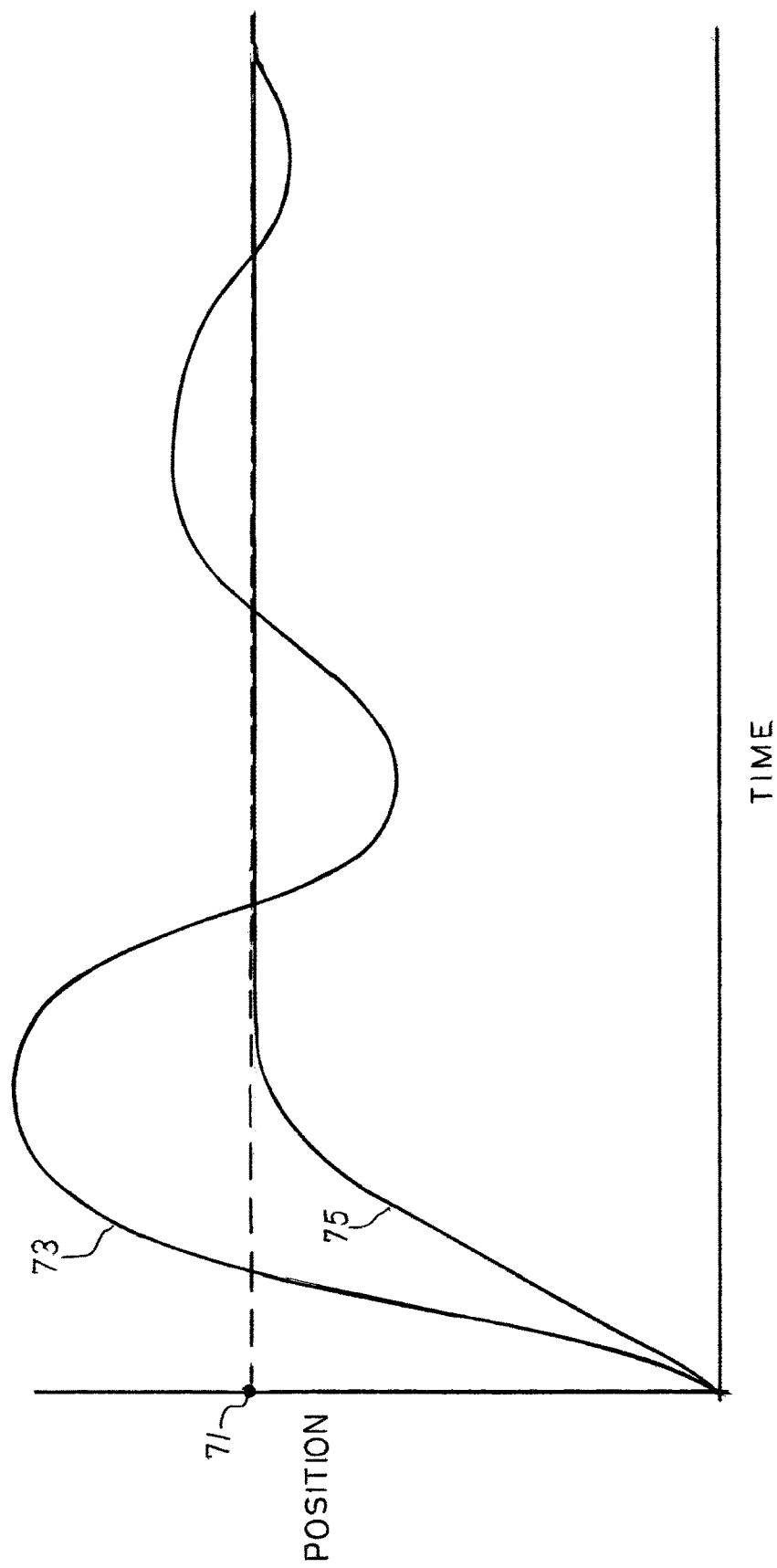
FIG. 9 is a graphical representation of shuttle position over time with and without eddy current dampening.
Figure 10:
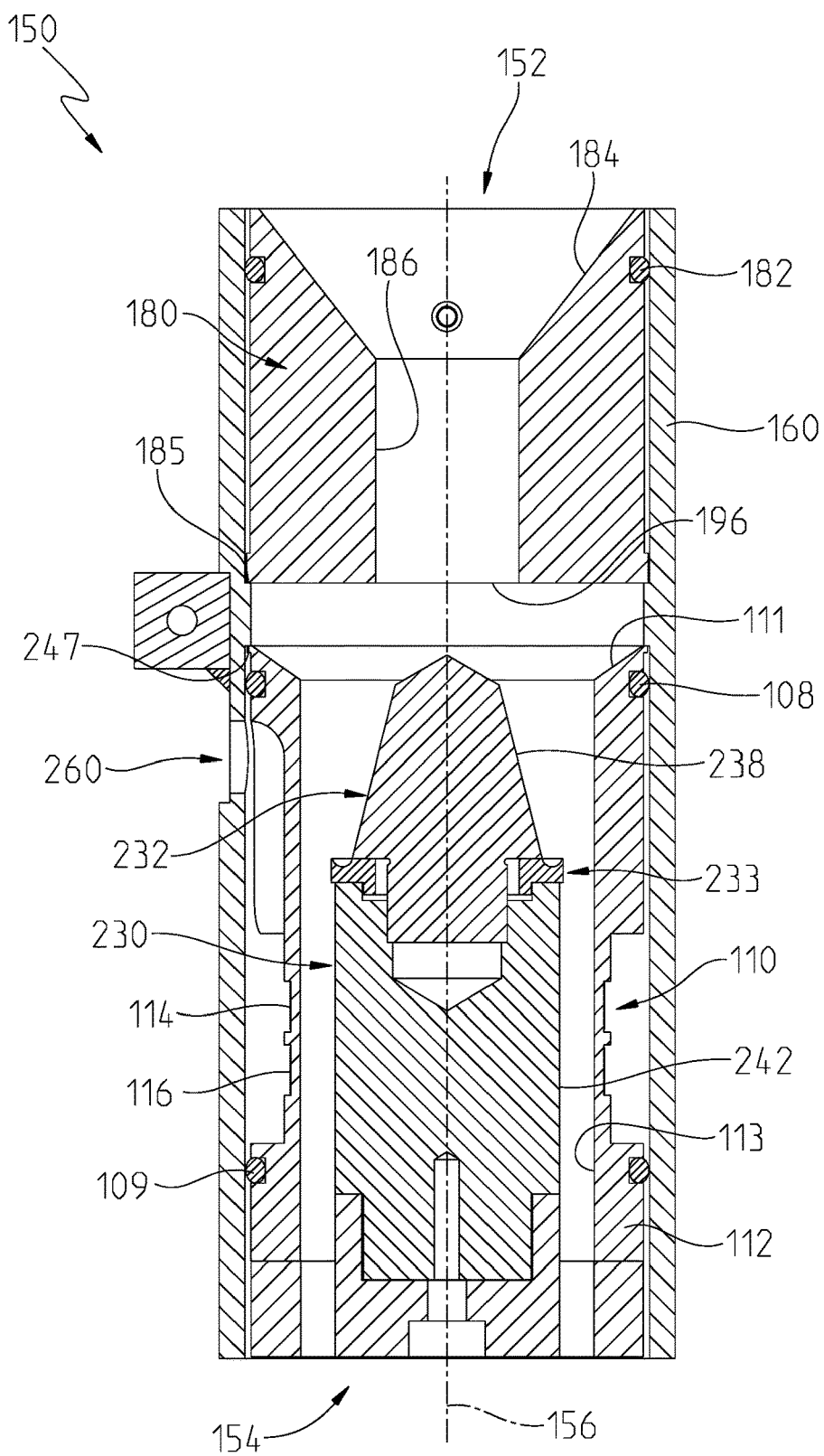
FIG. 10 is a side section view of a capacitive flow sensor.
Figure 11:
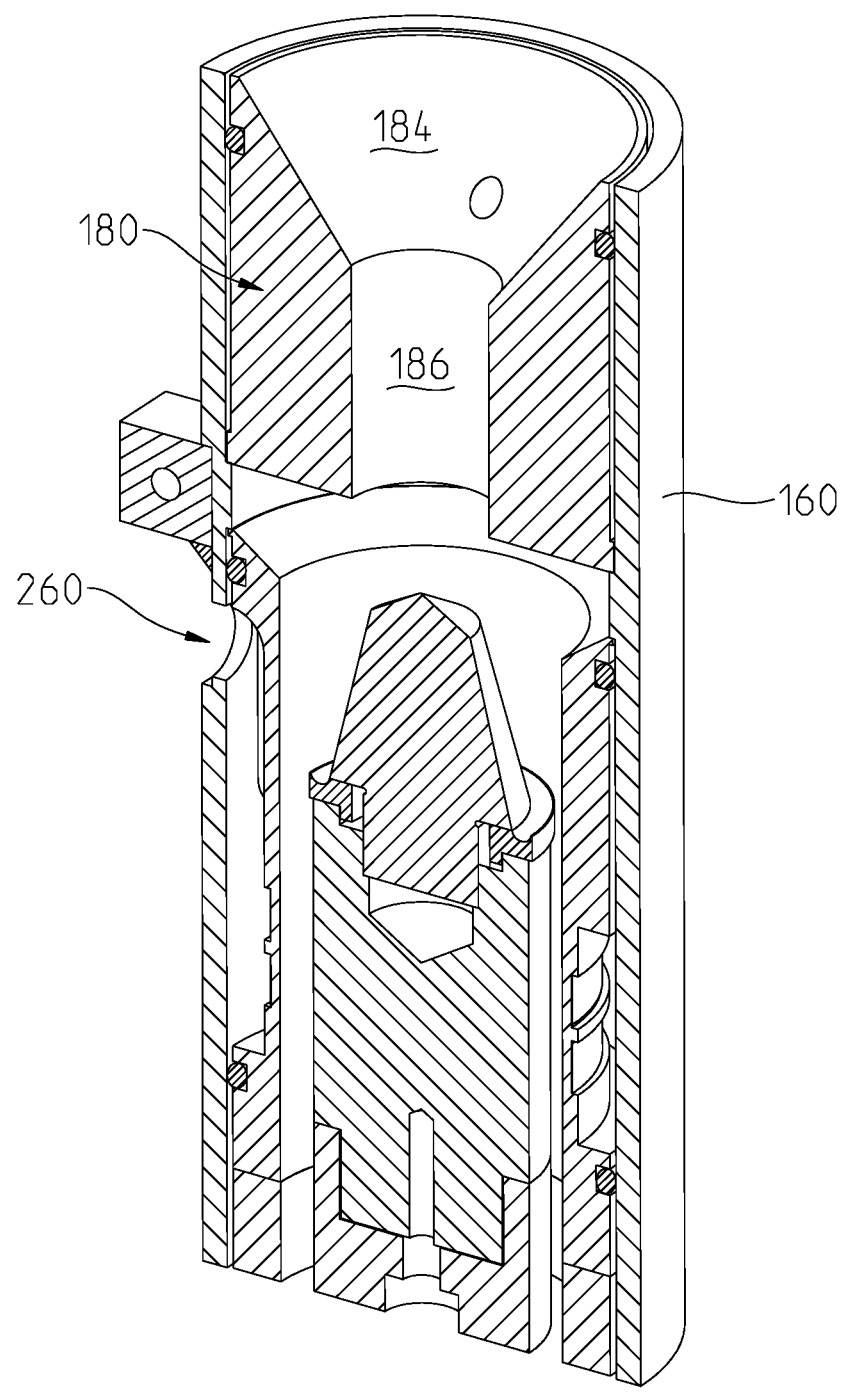
FIG. 11 is an isometric section view of the sensor in FIG. 10.
Figure 12:
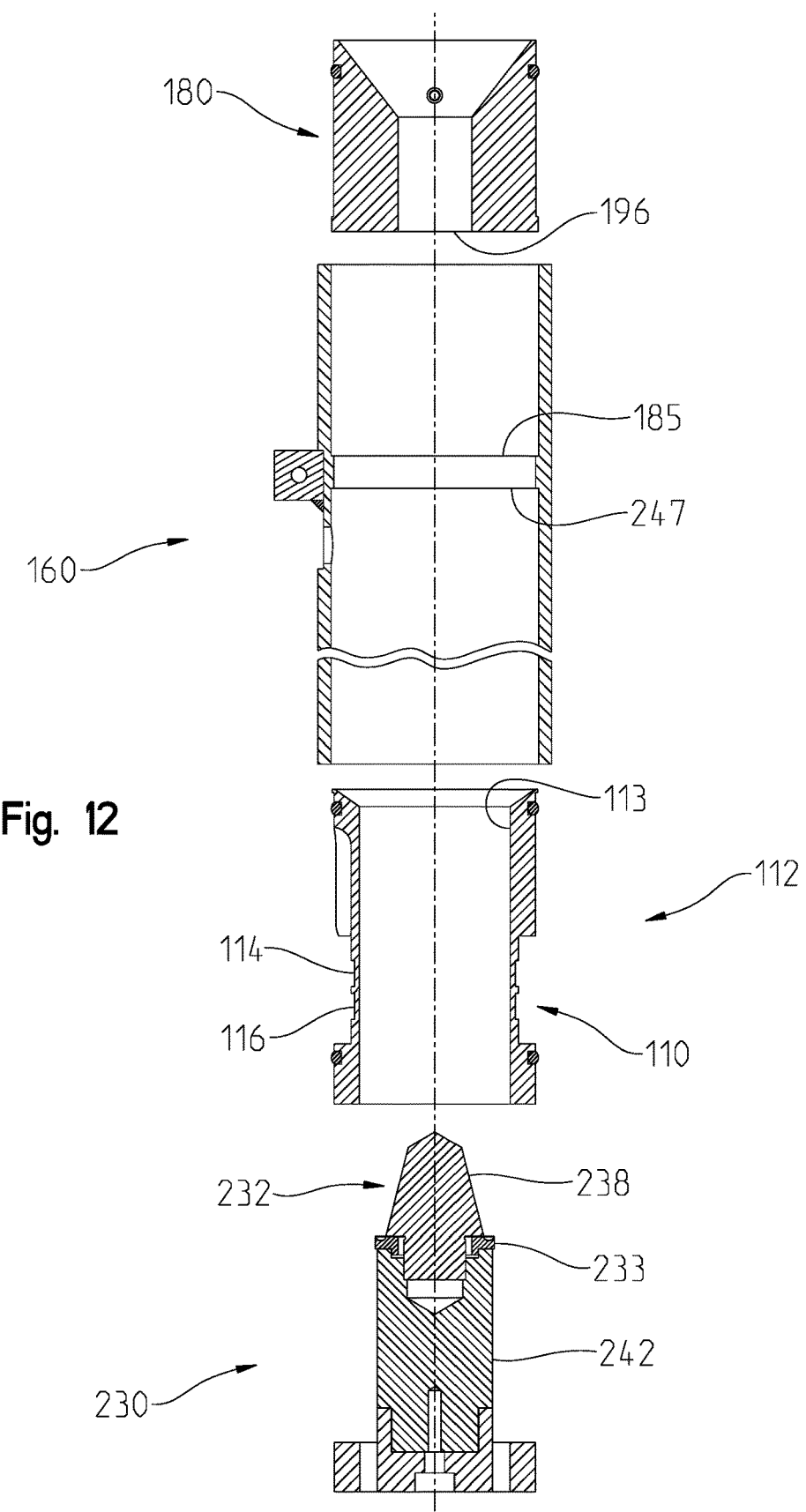
FIG. 12 is an exploded side section view of the sensor in FIG. 10.
Figure 13:
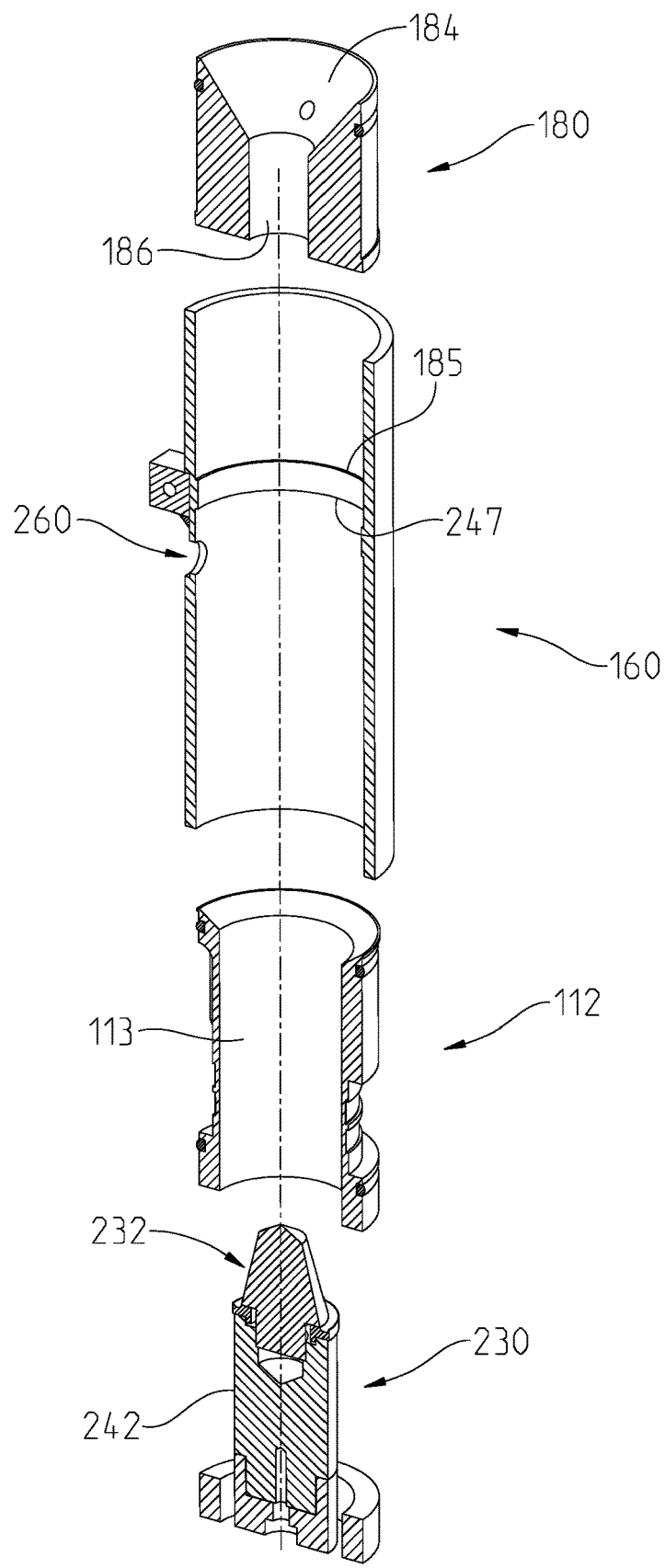
FIG. 13 is an exploded isometric side section view of the sensor in FIG. 10.

As previously mentioned, the tube 20 may be made from copper, aluminum, or a copper alloy, and the shuttle 70 has an array of shuttle magnets 72. Because the shuttle magnets 72 are in close proximity to the tube 20, any movement of the shuttle 70 creates eddy currents in the tube 20. Eddy currents are created when a magnet is moved with respect to a conductive metal, such as brass, copper, or aluminum. The tube 20 in the embodiment herein is described as brass but other materials are contemplated. The valve 10 takes advantage of the eddy currents and uses them to act as a dampening force on the shuttle 70. Without eddy currents, when the coil is first energized, the shuttle 70 would react in an underdamped fashion 73, where it would first overshoot its desired position 71 and then oscillate until it settles down to its desired position 71. In other words, the shuttle 70 would bounce back and forth before arriving at its desired position 71, represented in FIG. 9. Because the position of the shuttle 70 directly determines the amount of particulate media dispensed, overshoot and oscillation of the shuttle 70 would cause the particulate media to be dispensed unevenly, particularly when the valve 10 is first actuated or when the shuttle 70 is otherwise moved by the coil 32. Because of the eddy currents generated by the movement of the shuttle 70, overshoot and oscillation of the shuttle 70 are reduced or eliminated and the shuttle 70 responds in a damped fashion 75.

Figure 5A:
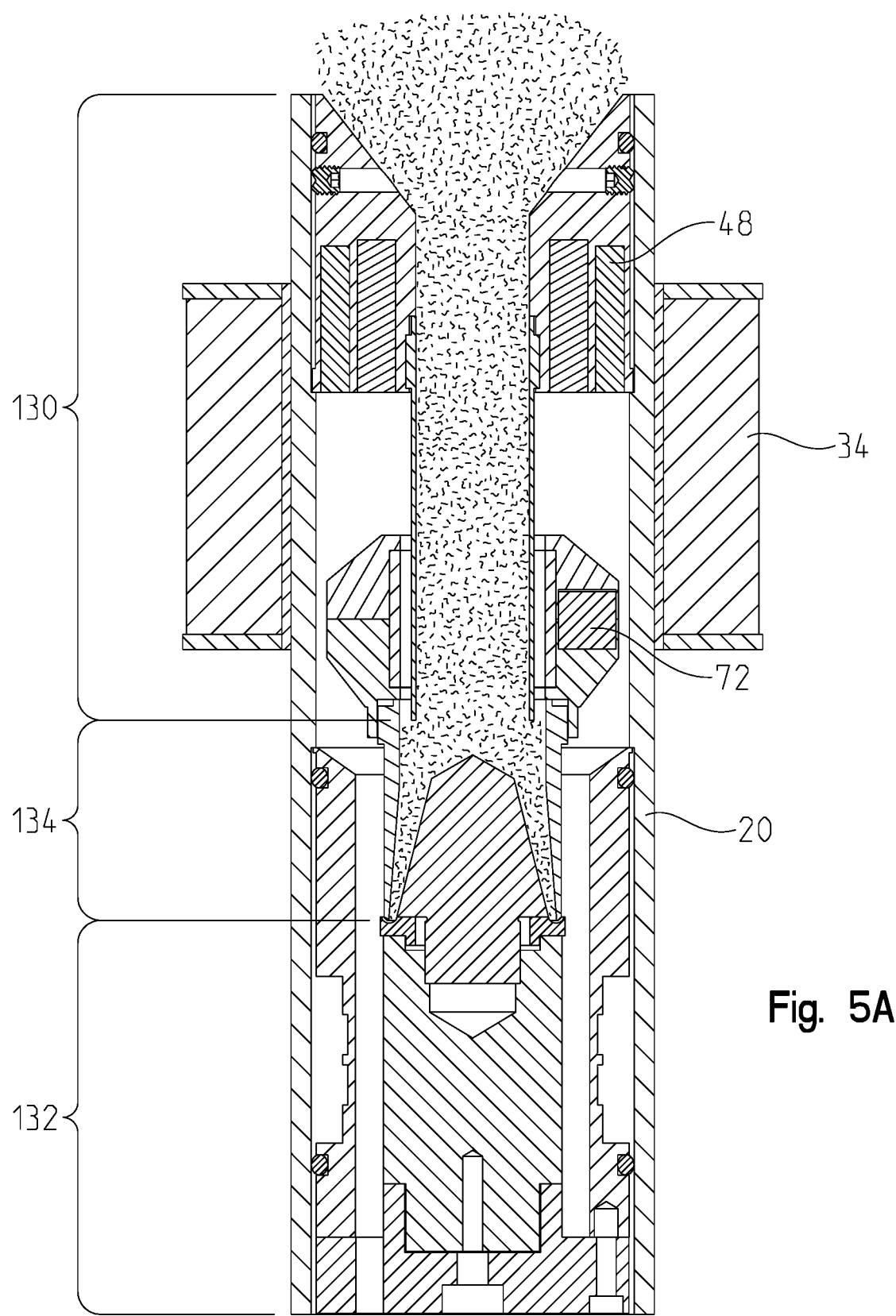
FIG. 5a is a section view 2-2 of the valve in the closed position and particulate media not being dispensed.
Figure 5B:
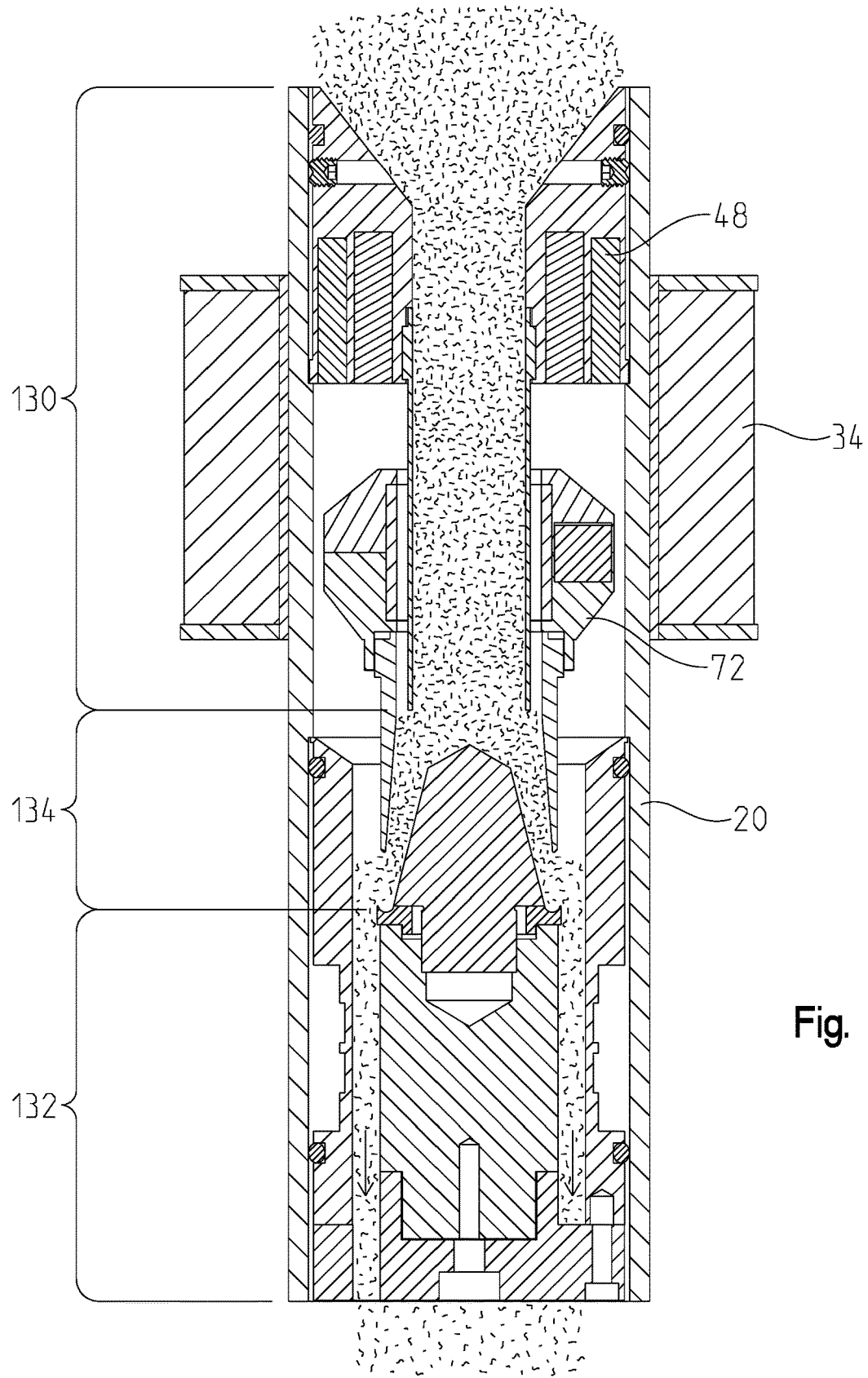
FIG. 5b is a section view 2-2 of the valve in the open position and particulate media being dispensed so that the flow path may be seen.
Figure 6:
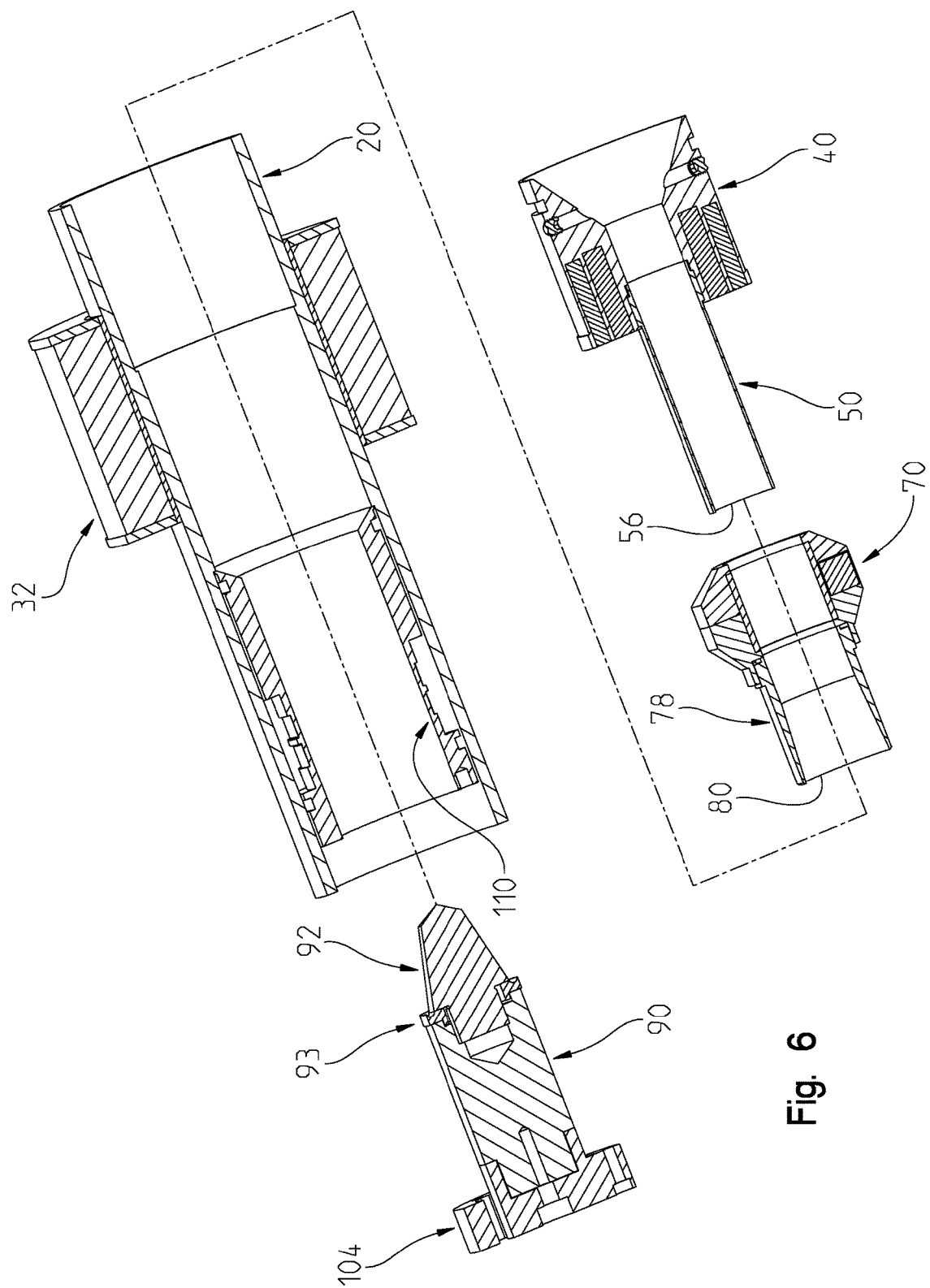
FIG. 6 is a section view of the valve as disassembled.
Figure 7:
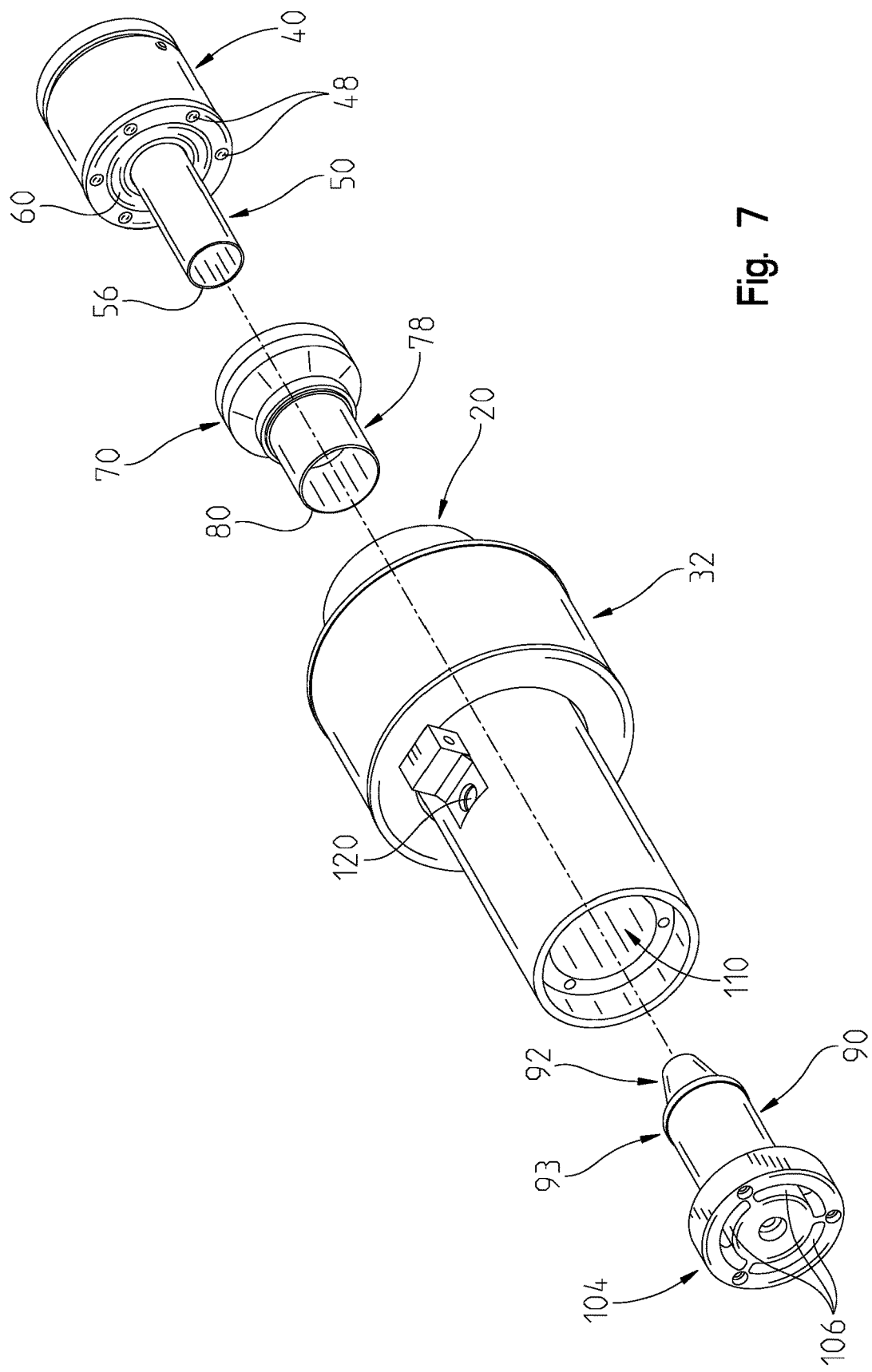
FIG. 7 is an isometric section view of the valve in FIG. 6.
Figure 8:
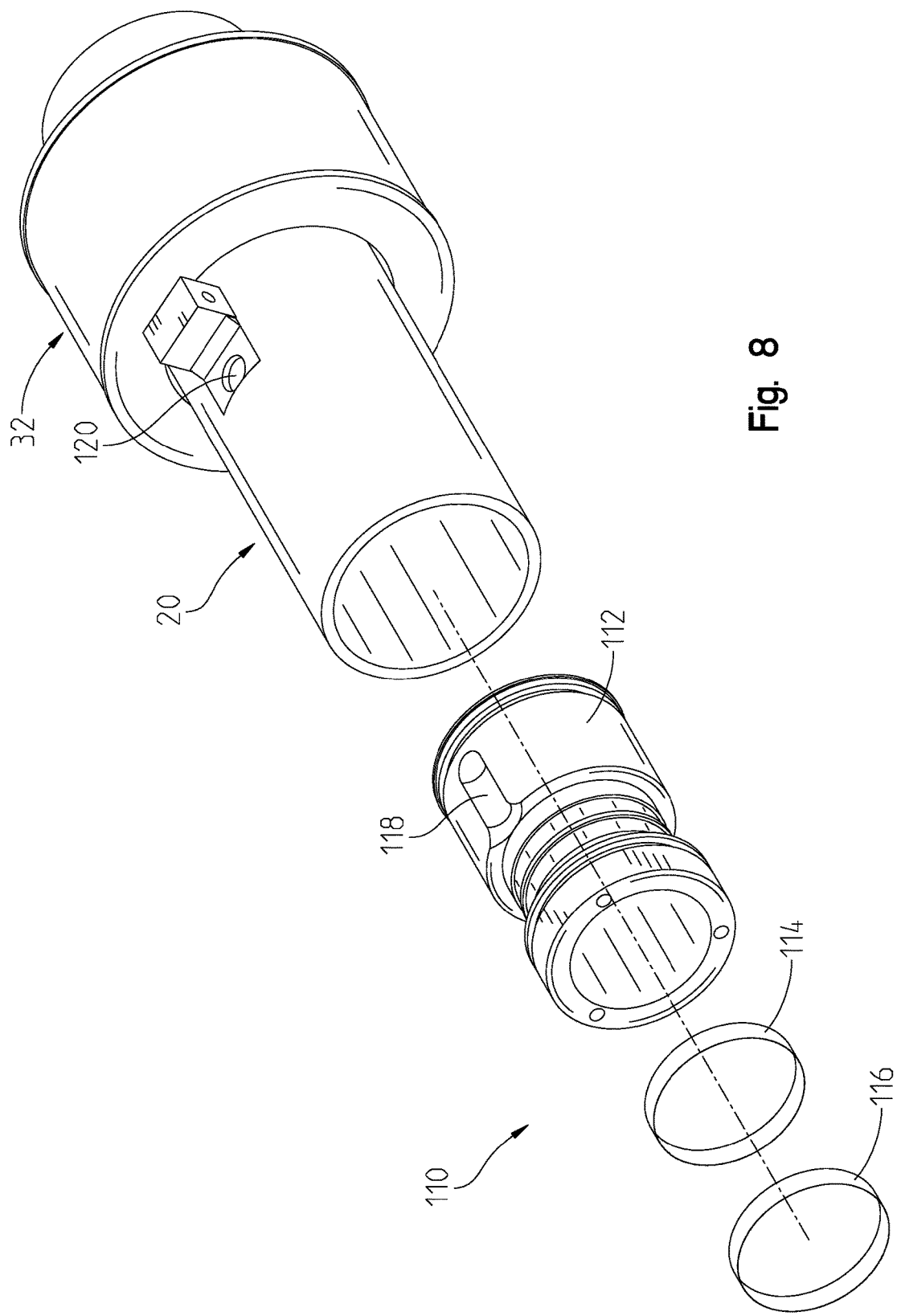
FIG. 8 is an exploded isometric view of the sensor and tube assembly.

The valve 10 is separated into several general chambers where the particulate can be present or flow through, shown in FIGS. 5A and 5B. The valve 10 is designed to be attached in a vertical orientation, with axis 16 being aligned with the force of gravity and have a supply of media present in the inlet chamber 130. The inlet chamber 130 starts at the top edge 22 of the tube 20 and is generally comprised of the internal volume inside of the funnel 40 and shuttle sleeve 50. The outlet and sensor chamber 132 is defined by the internal volume starting at the sealing surface 94, extending between the outer diameter surface 102 and inner diameter surface 113 of the sensor body 112, and terminating at the arcuate apertures 106. The outlet and sensor chamber 132 will only contain particulate while it is flowing through the valve 10, while the inlet chamber 130 will contain media regardless of flow. Located between the inlet chamber 130 and outlet and sensor chamber 132 is a center chamber 134 that is defined by the internal volume between the terminal edge 56 and terminal sealing edge 80. The internal volumes herein described are the areas inside the valve 10 that can hold and dispense media. The internal volumes make up the flow path through the valve 10. The media contacts the inside surfaces 82, 84 of the shuttle sleeve 78. The center chamber 134, like the inlet chamber 130, may have media regardless of flow. Media that is released when the shuttle 70 moves and separates the terminal sealing edge 80 from the sealing surface 94 passes through the outlet and sensor chamber 132 substantially unimpeded. The media located in the inlet chamber is tightly packed together, shown in FIG. 5A, while the dispensed media as it exits the center chamber 134 is entrained in a fluid (commonly air). As the media passes through the portion of the outlet and sensor chamber 132 that is surrounded by the flow sensor 110, the media is detected by the flow sensor 110. Because the outlet and sensor chamber 132 is encircled by the sensor rings 114, 116 at an equal distance, the media is reliably detected. Detection is further enhanced by having the flow diverter 90 predictably locate the media in a flow path very near the sensor rings 114, 116. The velocity of the dispensed media, as it passes the flow sensor 110 is predictable because the distance from the replaceable seal 93 to the sensor rings 114, 116 is fixed.

A capacitive flow sensor 150, as shown in FIGS. 10-14, may be used as a separate component to measure the flow of particulate that is located downstream of a flow valve. The flow sensor 150 shares many components as the valve 10, with some differences. The flow sensor 150 has an inlet 152 and an outlet 154. It includes a funnel 180 that directs the flow from the inlet 152 towards a central axis 156. The funnel 180 has an inside surface 184 that is angled, along with a cylindrical surface 186. The funnel 180 fits and is secured within the tube 160. It is sealed with an o-ring 182 and is seated on a step surface 185. As opposed to the funnel 40, the funnel 180 is shown without any magnets or magnetic shields. The funnel 180 forms an inlet chamber 270 of the flow sensor 150 that is between the inlet 152 and a terminal edge 196 of the cylindrical surface 186.

Located on the central axis 156 is a fixed flow director 230 that is affixed to the tube 160 near the outlet 154. The fixed flow director 230 has an outer surface 242 and is shown as cylindrical. The fixed flow director 230 has a cone portion 232 and may have a conical surface 238. It is contemplated that the cone portion 232 is removable for replacement or can be exchanged with a differently contoured outer surface to change the flow properties. It is further contemplated that a flow disrupting ring 233 is held on the fixed flow director 230 by the cone portion 232. The disrupting ring 233 may include a surface contour to further refine the flow of the media. The outer surface 242 has a larger diameter than the cylindrical surface 186.

Figure 14:
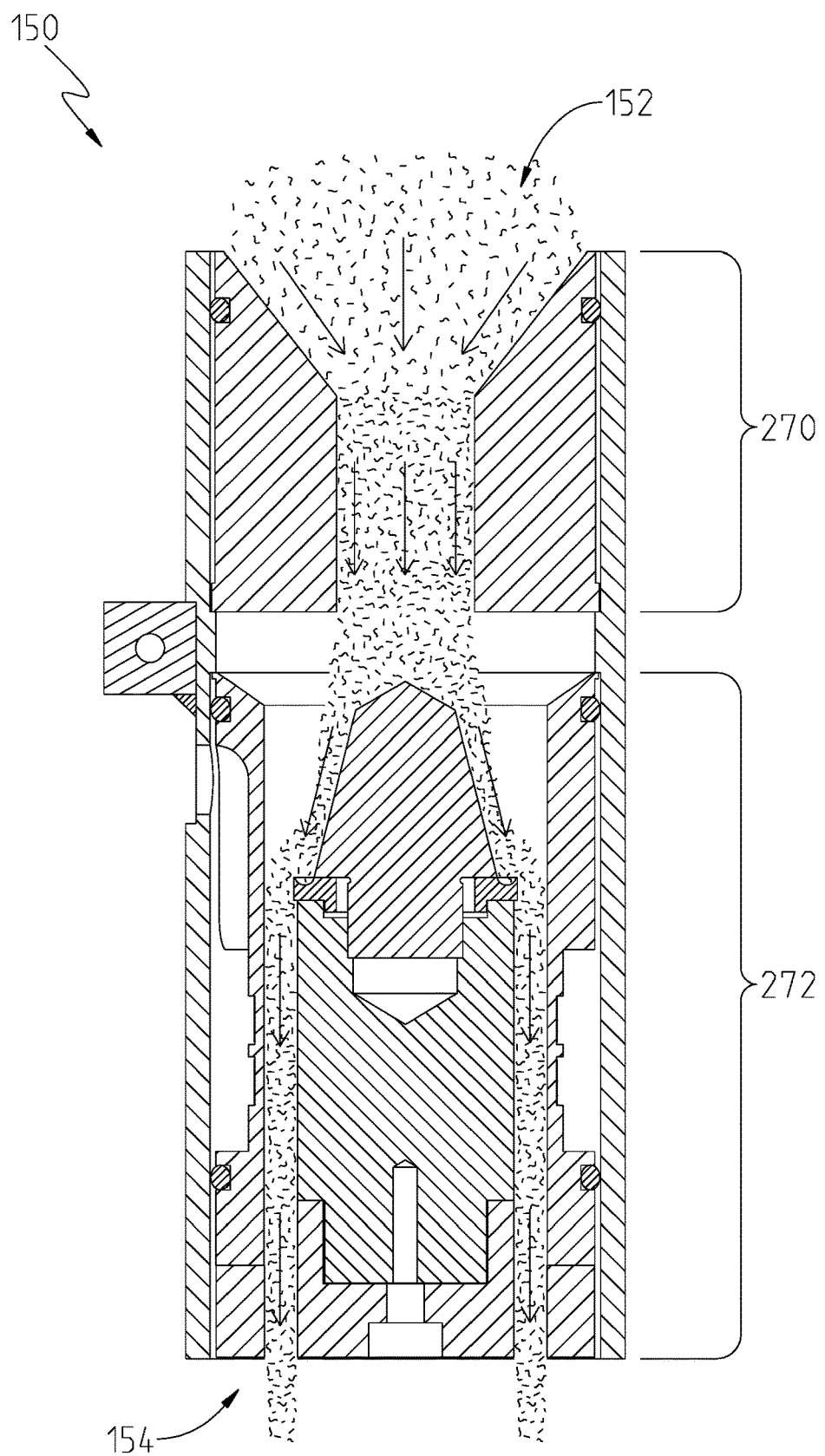
FIG. 14 is a side section view of the sensor in FIG. 10 showing the flow of media therethrough.

Surrounding the fixed flow director 230 is the flow sensor 110 as previously described. The flow sensor 110 is secured in the tube 160 where it is sealed with o-rings 108, 109 and abuts a step 247 in the tube 160. The tube 160 has a wire egress 260 where the sensor wires (not shown) can pass through to be connected to signal conditioning circuitry, other electronics, or a valve located upstream. The fixed flow director 230 and flow sensor are located in the outlet portion 272 as shown in FIG. 14. The fixed flow director 230 directs particulate media from the center or central region of the tube and towards the inner diameter surface 113 of the sensor body 112.

The flow sensor measures the quantity of particulate present at the sensor rings 114, 116. With the media falling at a consistent velocity and free-flowing through the outlet 154, the higher the density, the more particulate being dispensed. However, as a standalone sensor, the velocity of the media as it enters the inlet can vary for several reasons. First, the vertical distance between the sensor 150 and the upstream dispensing valve (not shown) causes the media to accelerate. For different types of media, the velocity of the media at the inlet 152 can vary based on the physical properties, such as the size, shape, and type of material that makes up the media. To normalize the velocity of the media, the funnel 180 and fixed flow director 230 cooperate to create a tortuous, winding, zigzag, or otherwise indirect flow path between the inlet 152 and outlet 154. The flow sensor 150 is designed to be installed in a vertical orientation with the central axis 156 aligned with the earth's gravity. Some misalignment is tolerated, but the flow of particulate through the sensor 150 is from gravity and uneven flow may occur as the central axis 156 is out of alignment. As particulate media enters the inlet chamber 270, any media that is farther away from the central axis 156 than the cylindrical surface 186 will contact the inside surface 184. The media that contacts the inside surface 184 will change direction. The angle of the inside surface 184 directs any media that contacts it towards the central axis 156. The media then continues to fall through the funnel 180 and is surrounded by the cylindrical surface 186. The height of the cylindrical surface 186 creates conditions that encourage laminar flow of the particulate. It is contemplated that the cylindrical surface 186 is shorter to allow more turbulent flow of the particulate. As the particulate passes the funnel 180, it contacts the fixed flow director 230, particularly the cone portion 232. Because the fixed flow director 230 is larger than the cylindrical surface 186, all or nearly all of the particulate will contact the fixed flow director 230. This causes the particulate to change direction and slow. The speed of the particulate as it enters the sensor 150 may vary or have particles that are moving faster than other particles. For accurate sensing, the particles need to be traveling at a consistent speed. The funnel 180 and fixed flow director 230 prevent any particulate from passing through the sensor 150 without contacting at least one surface.

It is understood that while certain aspects of the disclosed subject matter have been shown and described, the disclosed subject matter is not limited thereto and encompasses various other embodiments and aspects. No specific limitation with respect to the specific embodiments disclosed herein is intended or should be inferred. Modifications may be made to the disclosed subject matter as set forth in the following claims.

What is claimed is:
1. An inline device for sensing particulate, said device comprising:
   a tube having an inlet and an outlet;
   a funnel located within an inlet portion and fixed with respect to said tube adjacent said inlet, said funnel for receiving said particulate from said inlet and directing said particulate towards a central axis;
   a fixed flow director located within an outlet portion and fixed with respect to said tube, said fixed flow director centered about said central axis and having an outer diameter, said outer diameter of said fixed flow director being larger than an inside diameter of said funnel;
   a capacitive sensor located within said outlet portion and fixed with respect to said tube, said capacitive sensor having an inside diameter surrounding said fixed flow director, said capacitive sensor having a first sensor ring and a second sensor ring adjacent thereto, said first and second sensor rings for circumscribing said particulate flowing around said fixed flow director; and said fixed flow director directing said particulate away from said central axis and towards said inside diameter of said capacitive sensor, said funnel and said fixed flow director cooperating to form an uninterrupted indirect flow path through said device from said inlet to said outlet, said capacitive sensor surrounding said indirect flow path and said flow director directing said particulate in said indirect flow path toward said capacitive sensor.

2. The device in claim 1, wherein said funnel having a cylindrical portion, said inside diameter of said funnel being located on said cylindrical portion.

3. The device in claim 1, wherein said indirect flow path creating a consistent velocity of said particulate when said particulate passes through said first and second sensor rings.

4. The device in claim 1, wherein said fixed flow director having a tapered cone portion.

5. The device in claim 4, wherein said flow director having a disrupting ring to induce turbulence in said particulate when said particulate flows around said flow director.

6. The device in claim 1, wherein said capacitive sensor has a sensor body affixed to said tube, said first and said second sensor rings affixed to said sensor body, said inside diameter located on said sensor body, said capacitive sensor having a channel to guide wires from said sensor rings to a wire egress in said tube.

7. The device in claim 1, wherein said fixed flow director supported by a mounting base having arcuate apertures, said mounting base affixed to said tube.

8. The device in claim 1, wherein said fixed flow director encouraging laminar flow of said particulate as said particulate passes said capacitive sensor.

9. A device for sensing particulate, said device comprising:

an inlet portion having an inlet chamber, said inlet chamber extending from an inlet to a terminal edge, said inlet chamber having a funnel to direct said particulate from said inlet towards a central axis;

an outlet portion having an outlet chamber extending from a lead-in surface on a sensor body to an outlet, said outlet portion including a cylindrical flow director fixed with respect to said sensor body for directing said particulate away from a central region of said outlet portion, said outlet portion including a capacitive sensor having said sensor body with a cylindrical inside surface surrounding said cylindrical flow director, said sensor body having a first sensor ring and a second sensor ring affixed thereto, said cylindrical flow director and said cylindrical inside surface forming an annular flow path, said particulate passing through said annular flow path; and a tube surrounding said inlet chamber and said outlet chamber, said tube connecting said chambers.

10. The device in claim 9, wherein said capacitive sensor having a channel to guide wires from said first and second sensor rings to a wire egress in said tube.

11. The device in claim 9, wherein said cylindrical flow director is supported by a mounting base having arcuate apertures, said mounting base affixed to said tube.

12. The device in claim 9, wherein said cylindrical flow director having a cone portion.

13. The device in claim 12, said cylindrical flow director having a disrupting ring to induce turbulence in said particulate when said particulate flows around said cylindrical flow director.

14. A device for capacitively sensing the flow of particulate, said device comprising:

an inlet portion having an inlet chamber, said inlet chamber extending from an inlet to a terminal edge, said inlet chamber having a funnel to direct particulate from said inlet towards a central axis;

an outlet portion including a fixed flow director for directing said particulate away from a central region of said outlet portion, said outlet portion including a capacitive sensor having a first sensor ring and a second sensor ring adjacent thereto and fixed with respect to said fixed flow director, said fixed flow director being cylindrical, said capacitive sensor located in a sensor body having an inside surface facing said fixed flow director, said inside surface cooperating with said fixed flow director to define an annular flow path; and a tube surrounding said inlet chamber and said outlet portion, said tube connecting said portions, said inlet chamber and said funnel having a larger diameter near a top edge and narrowing to a smaller diameter towards said fixed flow director.

15. The device in claim 14, wherein said capacitive sensor having a sensor body affixed to said tube and having said first sensor ring and said second sensor ring affixed to said sensor body, said sensor body having an inside diameter located thereon.

16. The device in claim 15, wherein said capacitive sensor having a channel to guide wires from said first and second sensor rings to a wire egress in said tube.

17. The device in claim 14, wherein said fixed flow director supported by a mounting base having arcuate apertures, said mounting base affixed to said tube.

18. The device in claim 17, wherein said fixed flow director having a cone portion and a disrupting ring to induce turbulence in said particulate when said particulate flows around said flow director.

* * * * *